United States Patent [19]
Dieken et al.

[11] Patent Number: 5,347,583
[45] Date of Patent: Sep. 13, 1994

[54] ELECTRONIC STETHOSCOPE HAVING BINAURAL EARPIECE

[75] Inventors: Alan P. Dieken, Oakdale; Jon A. Kirschhoffer, White Bear Lake, both of Minn.

[73] Assignee: Minnesota Mining and Manufacturing Company, St. Paul, Minn.

[21] Appl. No.: 991,840

[22] Filed: Dec. 16, 1992

[51] Int. Cl.⁵ ............................................. A61B 7/04
[52] U.S. Cl. .................................................. 381/67
[58] Field of Search ................................ 381/67, 154

[56] References Cited

U.S. PATENT DOCUMENTS

| | | | |
|---|---|---|---|
| 2,115,478 | 4/1938 | von Baüssen | 381/67 |
| 3,555,187 | 1/1971 | Rowley | 381/67 |
| 3,790,712 | 2/1974 | Andries | 179/1 ST |
| 4,071,694 | 1/1978 | Pfeiffer | 179/1 ST |
| 4,072,822 | 2/1978 | Yamada | 381/67 |
| 4,170,717 | 10/1993 | Walshe | 179/1 ST |
| 4,254,302 | 3/1981 | Walshe | 179/1 ST |
| 4,440,258 | 4/1984 | Packard | 181/137 |
| 4,723,555 | 2/1988 | Shue | 128/715 |
| 4,783,813 | 11/1988 | Kempka | 381/67 |
| 4,878,501 | 11/1989 | Shue | 128/715 |
| 5,003,605 | 3/1991 | Phillipps et al. | 381/67 |

FOREIGN PATENT DOCUMENTS

| | | | |
|---|---|---|---|
| 2659007 | 9/1991 | France | 381/67 |

*Primary Examiner*—Forester W. Isen
*Attorney, Agent, or Firm*—Gary L. Griswold; Walter N. Kirn; William D. Bauer

[57] ABSTRACT

A binaural electronic stethoscope adapted to receive auscultatory sounds from a body and adapted to transmit the auscultatory sounds to a user. A chestpiece is adapted to be utilized in cooperation with the body. An acoustical transducer cooperates with the chestpiece and receives auscultatory sounds and transforms the auscultatory sounds into an electrical input signal. A signal processor processes the electrical input signal to produce an electrical output signal. A first tubular member couples the chestpiece to a housing. A speaker is mounted within the housing and converts the electrical output signal into an acoustical output signal. Second and third tubular members are coupled to the housing and are acoustically coupled to the speaker. First and second earpieces are coupled to the second and third tubular members, respectively, and receive the acoustical output signal and provide the acoustical output signal to the user. The first tubular member has an acoustical cavity acoustically coupled to the speaker in the housing. In this way, the acoustical cavity of the first tubular member and the second and third tubular members form a sound chamber both in front of and behind the speaker providing balanced acoustical response.

10 Claims, 4 Drawing Sheets

ELECTRONIC STETHOSCOPE HAVING BINAURAL EARPIECE

TECHNICAL FIELD

The present invention relates generally to electronic stethoscopes and, more particularly, to electronic stethoscopes having a binaural earpiece.

BACKGROUND OF THE INVENTION

Stethoscopes have long been used by physicians to monitor auscultatory sounds. Typically stethoscopes have been comprised of a head or chestpiece, a sound transmission mechanism and an earpiece assembly. The chestpiece is adapted to be placed near or against the skin, body, of a patient for gathering the auscultatory sounds. The sound transmission mechanism transmits the gathered sound to an earpiece, or a pair of earpieces called a binaural earpiece, where the physician or other health professional may monitor the sound.

Recently, some stethoscopes have utilized electronics for at least part of the sound processing path. In most of these devices, the auditory sound is picked up by a microphone usually located in a detection device which is similar to the chestpiece of a conventional acoustic stethoscope in external appearance. The electrical signal from the microphone is then processed electronically and is coupled to a speaker, or speakers, where the electrical signal is converted back into an auditory sound for reception by the physician. Of course, other electronic analysis or display of the auscultatory sounds may be performed by the signal processor, in addition to the usual conversion back into an auditory sound.

The incorporation of electronic circuitry into the stethoscope has been a considerable design problem for the engineer. Typically, the electronic circuitry increases the physical size of the stethoscope package. Either the size of the chestpiece is increased in size dramatically or an additional enclosure to house the electronics is located between the chestpiece and earpiece assembly or both. In both of these cases, the resulting stethoscope is bulky, cumbersome to use and not easily storable between uses.

Further, the location of and housing of the electrical to acoustic transducer, or speaker, in the electronic stethoscope is a problem.

In one case, the speaker may be located in the chestpiece. In this case, the acoustic signal must then be routed through long tubes to eventually reach the user's ears. The physical distance which this acoustic signal must travel increases the amplification burden of the electronic stethoscope and increases the probability of contamination with unwanted and non-pertinent sounds.

In another case, the speaker may be located in either a separate housing or otherwise contained within tubular members near the user's ears. The advantage of this technique is to decrease the amount of amplification required and to decrease the likelihood of noise contamination. However, the disadvantage to this technique is that a severe acoustic restraint is placed on the speaker housing and/or a separate speaker must be used for each earpiece. Both of these items significantly limit the useability of the electronic stethoscope.

U.S. Pat. No. 3,790,712, Andries, Electronic Stethoscope System, describes an electronic stethoscope which has a chestpiece sized and shaped like a large rectangular, box which houses the electronic circuitry of the stethoscope. The box has a projecting member with a forward lip portion for engagement with a skin surface. A speaker is positioned in a housing located at the juncture of separate earpiece tubes. The housing in which the speaker is positioned is acoustically sealed from an electrical cord which electrically and mechanically couples the speaker housing to chestpiece (detection device).

U.S. Pat. No. 4,071,694, Pfeiffer, Stethoscope, describes a stethoscope which has both an electronic and an acoustic capability. The chestpiece of the stethoscope has a conventional shape and achieves a conventional function. A speaker/receiver is located at the bifurcation of the earpiece tubes and is connected by wires integral to the sound tube. This is a combination electronic-acoustic device thus the speaker is mounted to provide a bypass channel for sound under the purely acoustic mode of operation. The compartment containing the speaker/receiver is acoustically sealed from the flexible conduit coupling the speaker/receiver to the chestpiece.

U.S. Pat. No. 4,170,717, Walshe, Electronic Stethoscope, describes an electronic stethoscope which has a chestpiece having an elongated housing carrying a body piece which includes an annular ring to be placed against a patient's body. An electrical cord couples the chestpiece to a speaker positioned in a housing. The acoustic output of the speaker is coupled to a length of single tubing which, in turn, connects to a conventional binaural earpiece assembly.

U.S. Pat. No. 4,254,302, Walshe, Electronic Stethoscope, describes an electronic stethoscope having a chestpiece for acquiring auscultatory sounds from the body of a patient. A microphone for sound pickup and electronic signal processing equipment are located in the chestpiece. A flexible duct enclosing an electrical wire connects the chestpiece to an enclosure containing a small speaker. The speaker is acoustically isolated from the interior of the flexible duct connecting the speaker enclosure with the chestpiece. Another flexible duct of a specified length "h" acoustically couples the output of the speaker to a binaural earpiece assembly.

U.S. Pat. No. 4,723,555, Shue, Multi-Functional Radio/Wire Stethoscope Apparatus, and U.S. Pat. No. 4,878,501, Shue, Multi-Functional Radio/Wire Stethoscope Apparatus, describe an electronic stethoscope which has a chestpiece with a diaphragm on one side and a bell on the other designed for gathering visceral sounds. The electrical signal is provided to a wireless transmitter or to a speaker/earphone jack.

French Published Patent Application No. 2,659,007, Oclin et al, Stethoscope With Electronic Amplification, describes a stethoscope having [with] a microphone located in one sealed cavity and having a loudspeaker located in a second sealed cavity. The sealed cavity containing the loudspeaker is connected to the first sealed cavity containing the microphone by an electric conductor. The output of the loudspeaker acoustically communicates to a binaural earpiece.

SUMMARY OF THE INVENTION

A significant problem encountered by each of the aforementioned publications is that the speaker is positioned within a relatively small enclosure. This is, in part, due to the desire of locating the speaker close, or as close as possible, to the binaural earpiece assembly. In each of these publications, the acoustic environment of the speaker suffers significantly because there is no or relatively little volume of acoustic space behind the speaker. That is, the small speaker enclosure allows for no or little room on the side of the speaker cone which is opposite from the tube or tubes which are coupled directly to the earpieces. Constructed in this manner, the speaker cone is significantly restricted in its movement due to insufficient acoustic volume on the "back side" of the speaker.

The present invention provides an electronic stethoscope which provides a speaker in a small enclosure located near the binaural earpiece. However, instead of acoustically closing the speaker on the "back side", the present invention allows for acoustic communication from the speaker to an acoustical cavity formed by the interior of the tube mechanical coupling the speaker enclosure with the chestpiece of the stethoscope. The acoustical cavity allows the speaker to "breathe" by providing acoustical space both "in front of", i.e., from the speaker toward the earpieces, and "in back of", i.e., from the speaker back toward the chestpiece, the speaker.

In a typical binaural electronic stethoscope the electronic circuitry would limit the frequency response of the generated electrical signal to a range of 30 Hertz to 500 Hertz. In a typical example, it has been shown that providing the acoustical cavity of the present invention provides an improved low frequency, 30 Hertz to 50 Hertz, response of approximately 12 dB. This significantly increased low frequency response aids the physician or other health professional to obtaining an accurate representation of the desired auscultatory sound.

The present invention provides a binaural electronic stethoscope adapted to receive auscultatory sounds from a body and adapted to transmit the auscultatory sounds to a user. A chestpiece is adapted to be utilized in cooperation with the body. An acoustical transducer cooperating with the chestpiece for receiving the auscultatory sounds and transforming the auscultatory sounds into an electrical input signal. A signal processor processes the electrical input signal to produce an electrical output signal. A first tubular member couples the chestpiece to a housing. A speaker is mounted within the housing and converts the electrical output signal into an acoustical output signal. The speaker is electrically coupled to the electrical output signal. Second and third tubular members are coupled to the housing and are acoustically coupled to the speaker. First and second earpieces are coupled to the second and third tubular members, respectively, and receives the acoustical output signal and provides the acoustical output signal to the user. The first tubular member has an acoustical cavity acoustically coupled to the speaker in the housing. In this way, the acoustical cavity of the first tubular member and the second and third tubular members form a sound chamber both in front of and behind the speaker providing balanced acoustical response.

In a preferred embodiment, the acoustical cavity of the first tubular member is formed substantially over the entire length of the first tubular member. In a preferred embodiment, the acoustical cavity of the first tubular member is sealed from the chestpiece.

In one embodiment, the acoustical cavity of the first tubular member is open to the environment. In another embodiment, the acoustical cavity of the first tubular member is sealed from the environment.

In a preferred embodiment, the speaker has direct acoustic coupling to the second and third tubular member. In a preferred embodiment, the speaker is mounted within the housing with the axis of the speaker being substantially parallel with the axis of the first tubular member. In a preferred embodiment, the second and third tubular members have axis substantially orthogonal with the axis of the first tubular member. In a preferred embodiment, the second and third tubular members are substantially identical in size and shape. In a preferred embodiment, a low density acoustical material substantially fills the acoustical cavity of the first tubular member.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Electronic stethoscopes must provide acoustic response at least equal to their conventional acoustic counterparts. Electronic stethoscopes must also be similar to the weight, feel and ease of use of their conventional acoustic counterparts. In order for the physician to gain the most advantageous use of the stethoscope, the stethoscope should provide the highest possible clarity of auscultatory sound from the patient, body, as well as provide the greatest possible isolation from all extraneous sounds. In addition, electronic stethoscopes must offer sound isolation from the surroundings in which the stethoscopes is use.

Figure 1:
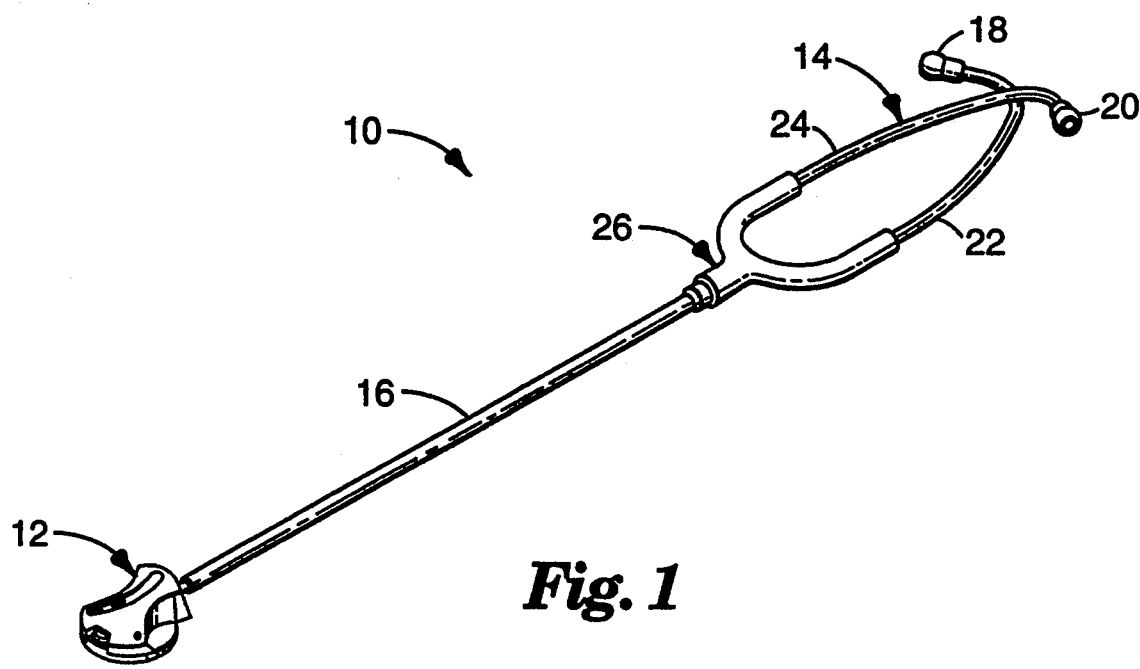
FIG. 1 is a perspective view of a stethoscope utilizing the binaural earpiece of the present invention.

Electronic stethoscope 10 illustrated in FIG. 1 consists of a chestpiece 12, or stethoscope head, a binaural assembly 14 and a connecting tube 16. The binaural assembly 14 has two earpieces 18 and 20 adapted to fit in or near the ear of a user, typically a physician or other medical professional. Earpiece tubes 22 and 24 are acoustically coupled to earpieces 18 and 20, respectively. Enclosure 26, located at juncture of tubes 22 and 24 with connecting tube 16, provides a location for a speaker 28 (not shown). Speaker 28 transforms the auscultatory sounds which are picked up by chestpiece 12 and transduced into and processed in the electrical domain back to the acoustic domain where earpiece tubes 22 and 24 transmit the acoustic sounds to earpieces 18 and 20, respectively.

Figure 2:
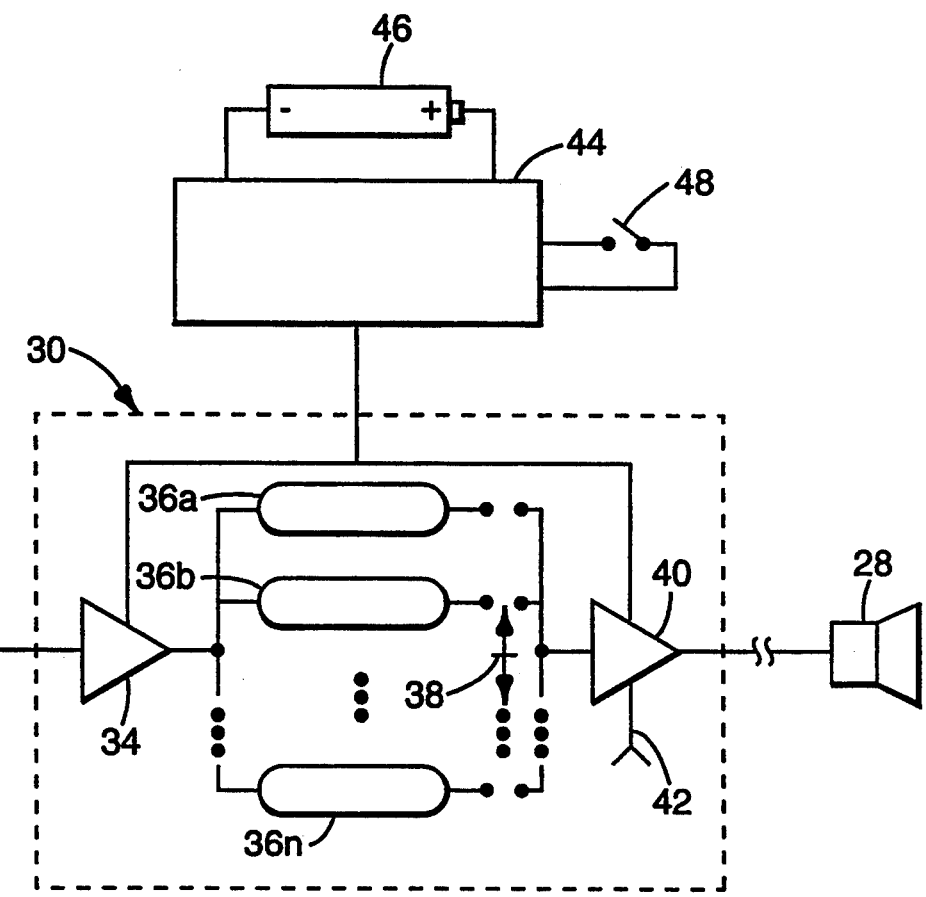
FIG. 2 is a functional block diagram of a stethoscope utilizing the present invention.

The sound transmission system of stethoscope 10 may be entirely electronic or may be a combination acoustic and electronic, or dual acoustic and electronic. A simplified block diagram of the electronic transmission system 30 is illustrated in FIG. 2. An acoustic to electronic transducer, a microphone, 32 would be located along the acoustic sound transmission path, typically in or very near the chestpiece 12, and even more typically positioned near the bottom surface of the chestpiece 12 so as to be near the source of auscultatory sounds. Preamplifier 34 receives the electrical signal from microphone 32 and provides an increased electrical signal to a plurality of signal processors having different transfer functions (36a, 36b . . . 36n). One or more transfer functions (36a, 36b . . . 36n) can be selected from switch 38. The processed electrical signal from the frequency band filters (36a, 36b . . . 36n) is then amplified and/or combined in power amplifier 40 which is controlled by volume control 42. Power to signal processor 30 is supplied by power supply circuit 44 with energy from battery 46. Power supply circuit 44 is controlled by power on/off switch 48. Typically, microphone 32, preamplifier 34, transfer functions (36a, 36b . . . 36n), switches 38 and 48, power amplifier 40, volume control 42, power supply 44 and battery 46 are all located within chestpiece 12. Speaker 32 is the only electrical component located outside of chestpiece 12.

Figure 3:
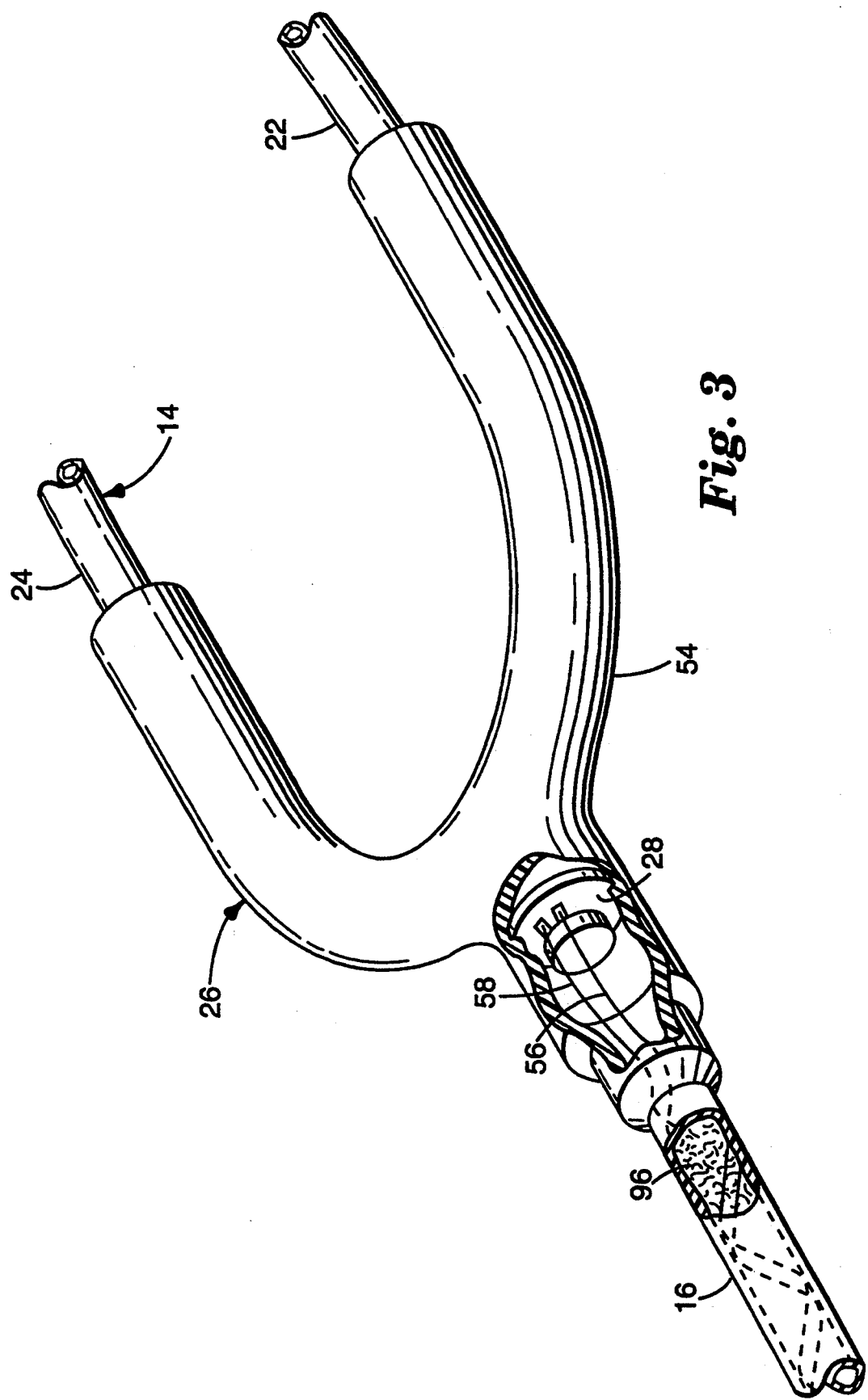
FIG. 3 is a detailed view of the speaker enclosure utilizable in the present invention.
Figure 4:
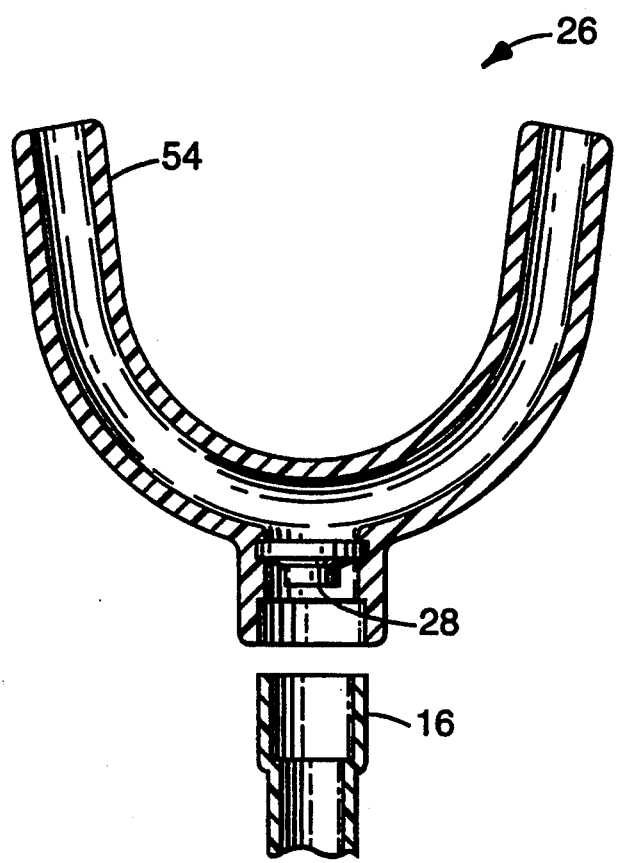
FIG. 4 is a cross-sectional view of the speaker enclosure of FIG. 3.

Detail of the enclosure 26 and other aspects associated with speaker 32 can be seen in FIGS. 3 and 4. Connecting tube 16 mechanically and electrically couples enclosure 26 to chestpiece 12 (FIG. 1 ). Enclosure 26 is, in turn, mechanically and acoustically coupled to earpiece tubes 22 and 24 which form a portion of binaural assembly 14. Preferably, enclosure 26 is formed integrally with connecting tube 16 and base 54. Base 54 is a molded "U-shaped" piece which provides openings at the top of each side of the "U" for earpiece tubes 22 and 24, respectively. Base 54 is molded with the top portion of enclosure 26 integral to a single molding. Similarly, the top portion of connecting tube 16 is molded to form the lower portion of enclosure 26 integral to a single molding. When the bottom end of base 54 is mated with the top end of connecting tube 16, enclosure 26 is created. Preferably, enclosure 26 forms a space which is somewhat larger (approximately 13.5 millimeters) than the interior diameter (6.35 millimeters) of connecting tube 16 and is sufficient to house speaker 28.

Speaker 28 is mounted within enclosure 26 on an axis which is substantially parallel to the longitudinal axis of connecting tube 16. Preferably, speaker 28 is sealed into enclosure 26 by the elastic force of the enclosure material without the aid of clips, gaskets. or "O" ring seals. In order to maximize sound reproducing qualities, speaker 28 is mounted near, or along, the centerline of connecting tube 16. Speaker 28 is electrically connected to the electronics contained in chestpiece 12 by electrical wires 56 and 58 which can be run inside of connecting tube 16. Speaker 28 is directly acoustically coupled into base 54 which, in turn, is directly acoustically coupled into earpiece tubes 22 and 24. Preferably, base 54 forms substantially a right angle with the sides of the "U" forming base 54.

Because of the tight space (enclosure 26) into which speaker 28 is mounted, its acoustical frequency response is limited. If the bottom portion of enclosure 26 were acoustically sealed from connecting tube 16, a very limited air space would be available on the back side of speaker 28 for the speaker cone to move. This limited space would, in turn, limit the low frequency response of speaker 28. It is, therefore, extremely important that speaker 28 be provided with an acoustical cavity on its back side to allow for movement of speaker cone in order to allow speaker 28 to achieve a greater low frequency response. Enclosure 26 is open to the interior of connecting tube 16. This opens a portion of, or the entire, length of connecting tube 16 for a volume of acoustical space to assist in the frequency response of speaker 28. Preferably, all, or substantially all, of the length of connecting tube 16 would be utilized for this purpose. The presence of electrical wires 56 and 58 within connecting tube 16 does not appreciably affect the acoustical cavity created within connecting tube 16. In one embodiment, connecting tube 16 is formed of polyvinylchloride, is approximately 50–60 centimeters long and has an interior diameter of approximately four millimeters.

It may be desirable to fill to acoustical cavity created within connecting tube 16 with a low density acoustical material for additional control of the low frequency acoustical impedance. Examples of such a low density acoustical material would be loosely packed fiberglass or polyester mating, Dacron 88 TM or Hollowfill TM available from E. I. Dupont de Demours, Inc. Further, the length of connecting tube 16 and presence of the low density acoustical material minimizes the possibility of ingress of ambient sound from the environment that would add noise to the intelligence transmitted to the physician or other health care professional.

Figure 5:
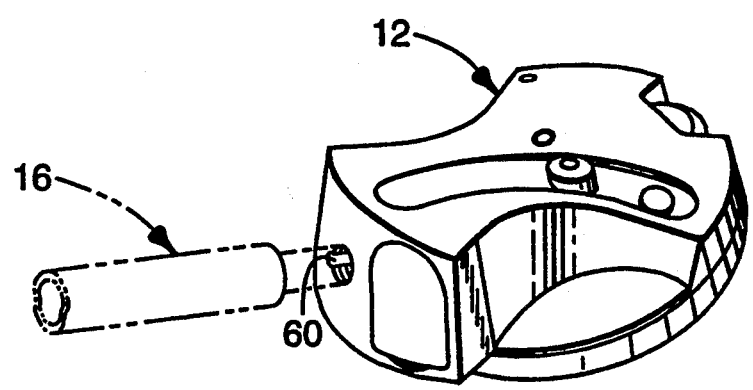
FIG. 5 is a more detailed view of the connection between the chestpiece and the connecting tube of one embodiment of the stethoscope of the present invention.

In some situations, it may be desirable to vent the acoustical cavity formed in connecting tube 16 to the environment or atmosphere. If this is desired, a vent 60 can be incorporated as shown in FIG. 5. Alternatively, the acoustical cavity formed in connecting tube 16 can be sealed from the environment or atmosphere, preferably being sealed at the juncture of connecting tube 16 with chestpiece 12.

The location of a single speaker 28 near to juncture of earpiece tubes 22 and 24 in base 54 provides the advantages of balanced acoustical loading on speaker 28 and assurance that the exact same acoustic intelligence is transmitted to both the left and the right ear of the physician or other health care professional using the stethoscope. This assurance is aided when the arms of base 54 are identically formed, sized and shaped and when earpiece tubes 22 and 24 are identically formed, sized and shaped.

The acoustical output loading of speaker 28 is matched with the electrical characteristics of the speaker by the design selection of size and length for the earpiece tubes 22 and 24. The acoustical unloading of the speaker diaphragm is precisely matched by the size and length of connecting tube 16. The acoustical impedance matching is accomplished by frequency response analysis.

Speaker 28 has impedance in the range of 1.6 to 32 ohms, preferably a 32 ohm two wire miniature "EarBud" speaker 13.6 millimeters in diameter supplied by Chia-Ping Enterprises Company LTD, Taipei, Taiwan. It is positioned and sealed in place, at the periphery of the speaker, in enclosure 26 to prevent sound leakage. Base 54 is sealed into the top end of connecting tube 16 forming enclosure 26. Connecting tube 16 and base 54 are all made of dip molded polyvinylchloride and sealed with VC 1 vinyl adhesive, available from Schwartz Chemical Company, New York.

Figure 6:
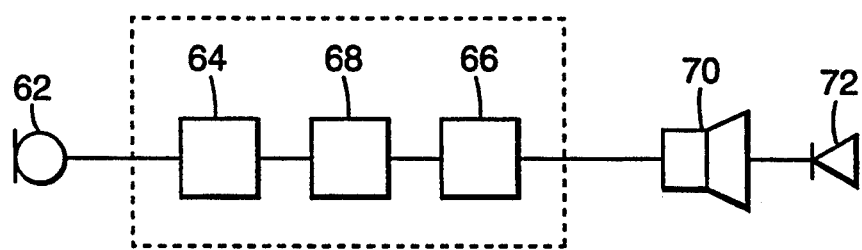
FIG. 6 is a simplified block diagram of a typical electronic stethoscope signal processing path.

An illustration of the advantageous result of the use of the present invention is illustrated in FIGS. 6 and 7. FIG. 6 illustrates, in block diagram form, a simplified, yet generally typical, signal path through an electronic stethoscope which processes the electrical signal by a the transfer function designed as an analog of the "diaphragm" response of a conventional acoustical stethoscope which is well understood and recognized by doctors and other health care professionals. A microphone 62 receives the auscultatory sound and converts the auditory signal into an electrical signal. The electrical signal then passes through signal processor 60 which includes low frequency cut off filter 64, set to roll off at approximately 20 Hertz; shaping element 68, providing the appropriate transfer function; and high frequency cut off filter 66, which is set to roll off at approximately 600 Hertz. The normal ear is generally insensitive to sound below 20 Hertz and virtually all body sounds of interest have no significant frequency content above 600 Hertz, with some prosthetic heart valve exceptions. The sharp low frequency roll off eliminates low frequency noise for example DC voltage bias and transient noise caused by moving the chestpiece across the body surface. The sharp high frequency roll-off rejects ambient environmental noise for example the human voice.

The output signal from signal processor 60 is amplified by power amplifier 70 and the amplified signal is then converted back into the acoustic domain by speaker 72.

Figure 7A:
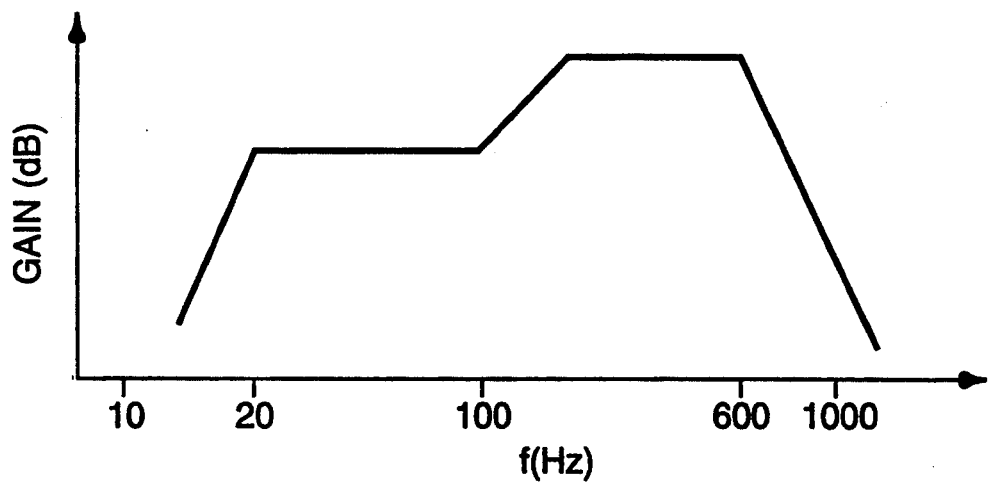
FIGS. 7A and 7B are diagrams illustrating the improved frequency response of the electronic stethoscope of the present invention.
Figure 7B:
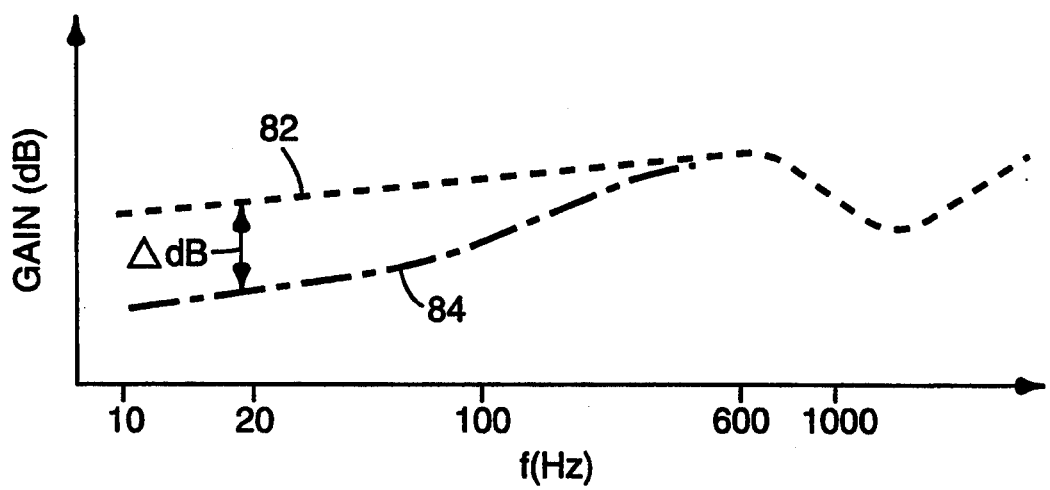

The output of signal processor 60 is shown diagrammatically in FIG. 7A where signal amplitude is plotted as a function of frequency. Line 80 in the diagram illustrates the frequency characteristics of the desired sound output which is the analog of the conventional acoustical stethoscope between approximately 20 Hertz and 600 Hertz. However, the actual frequency spectrum transmitted as sound to the ears of the user is a function of both the electronics including amplifier 70, signal shaping element 68 and filters 64, 66 of the stethoscope and the speaker 72. Speaker 72 is a electro-mechanical transducer with provides acoustic output constrained by the physical characteristics of the stethoscope limiting the frequency response. In FIG. 7B, line 82 illustrates the frequency response with an electronic stethoscope which utilizes the techniques of the presently claimed invention. In FIG. 7B, line 84 illustrates the frequency response of a similar electronic stethoscope which does not have the claimed features of the present invention. As can be seen in FIG. 7B, line 82 represents an improvement in low frequency response of approximately 12 dB over the frequency response represented by Line 80 at the low end of the useful frequency range. This substantially improved frequency response is the direct result of the application of the principles of the presently claimed invention.

Thus, it can be seen that there has been shown and described a novel electronic stethoscope having a unique binaural earpiece. It is to be recognized and understood, however, that various changes, modifications and substitutions in the form and the details of the present invention may be made by those skilled in the art without departing from the scope of the invention as defined by the following claims.

What is claimed is:

1. A binaural electronic stethoscope adapted to receive auscultatory sounds from a body and adapted to transmit said auscultatory sounds to a user, comprising:
   a chestpiece adapted to utilized in cooperation with said body;
   an acoustical transducer cooperating with said chestpiece for receiving said auscultatory sounds and transforming said auscultatory sounds into an electrical input signal;
   signal processing means being operatively coupled to said acoustical transducer for processing said electrical input signal to produce an electrical output signal;
   a housing;
   first tubular means coupling said chestpiece to said housing;
   speaker means mounted within said housing for converting said electrical output signal into an acoustical output signal;
   electrical connection means for coupling said electrical output signal to said speaker;
   second and third tubular means coupled to said housing and acoustically coupled to said speaker for acoustically transmitting said acoustical output signal;
   first and second earpieces coupled to said second and third tubular means, respectively, for receiving said acoustical output signal and providing said acoustical output signal to said user;
   said first tubular means having an acoustical cavity which is acoustically coupled to said speaker in said housing, said first tubular means forming an acoustic cavity which enhances the frequency response of said speaker;
   whereby said acoustical cavity of said first tubular means and said second and third tubular means form sound channels both in front of and behind said speaker providing balanced acoustical response.

2. A binaural electronic stethoscope as in claim 1 wherein said acoustical cavity of said first tubular member is formed substantially over the entire length of said first tubular member.

3. A binaural electronic stethoscope as in claim 2 wherein said acoustical cavity of said first tubular member is sealed from said chestpiece.

4. A binaural electronic stethoscope as in claim 3 wherein said stethoscope operates in an environment and wherein said acoustical cavity of said first tubular member is open to the environment.

5. A binaural electronic stethoscope as in claim 3 wherein said stethoscope operates in an environment and wherein said acoustical cavity of said first tubular member is sealed from the environment.

6. A binaural electronic stethoscope as in claim 2 wherein said speaker has direct acoustic coupling to said second and third tubular means.

7. A binaural electronic stethoscope as in claim 1 wherein said speaker has an axis extending along a direction of projection of sound from said speaker and wherein said speaker is mounted within said housing with said axis of said speaker being substantially parallel with the axis of said first tubular member.

8. A binaural electronic stethoscope as in claim 7 wherein said second and third tubular members have axis substantially orthogonal with said axis of said first tubular member.

9. A binaural electronic stethoscope as in claim 8 wherein said second and third tubular members are substantially identical in size and shape.

10. A binaural electronic stethoscope as in claim 1 further comprising a low density acoustical material substantially filling said acoustical cavity of said first tubular member.

* * * * *

UNITED STATES PATENT AND TRADEMARK OFFICE
CERTIFICATE OF CORRECTION

PATENT NO. : 5,347,583
DATED : September 13, 1994
INVENTOR(S) : Dieken et al.

It is certified that error appears in the above-indentified patent and that said Letters Patent is hereby corrected as shown below:

Column 6, line 53, delete "1.6" and insert therefor --16--.

Signed and Sealed this

Seventeenth Day of January, 1995

Attest:

BRUCE LEHMAN

*Attesting Officer*  *Commissioner of Patents and Trademarks*